United States Patent
Gencarelli

(10) Patent No.: US 8,226,564 B2
(45) Date of Patent: Jul. 24, 2012

(54) HANDPIECE FOR ULTRASONIC ELECTRO-MEDICAL APPARATUSES

(75) Inventor: Giuseppe Gencarelli, Milan (IT)

(73) Assignee: Italia Medica S.p.A., Milan (IT)

( * ) Notice: Subject to any disclaimer, the term of this patent is extended or adjusted under 35 U.S.C. 154(b) by 1310 days.

(21) Appl. No.: 11/816,886

(22) PCT Filed: Feb. 21, 2006

(86) PCT No.: PCT/IB2006/000340
§ 371 (c)(1),
(2), (4) Date: Aug. 22, 2007

(87) PCT Pub. No.: WO2006/090230
PCT Pub. Date: Aug. 31, 2006

(65) Prior Publication Data
US 2008/0255450 A1    Oct. 16, 2008

(30) Foreign Application Priority Data

Feb. 24, 2005    (IT) .............................. BO2005A0096

(51) Int. Cl.
*A61B 8/00*    (2006.01)
(52) U.S. Cl. ..................... 600/459; 601/2; 601/3; 601/4

(58) Field of Classification Search ................... 600/437, 600/459; 601/2–4; 604/22
See application file for complete search history.

(56) References Cited

U.S. PATENT DOCUMENTS 5,076,276 A * 12/1991 Sakurai et al. ................... 601/2
2003/0073055 A1    4/2003 Pollack et al.

FOREIGN PATENT DOCUMENTS

| EP | 0642769 A | 3/1995 |
|---|---|---|
| EP | 1103232 A | 5/2001 |
| EP | 1466648 A | 10/2004 |

OTHER PUBLICATIONS

International Search Report.

\* cited by examiner

*Primary Examiner* — Tse Chen
*Assistant Examiner* — Peter Luong
(74) *Attorney, Agent, or Firm* — William J. Sapone; Coleman Sudol Sapone P.C.

(57) ABSTRACT

The proposed handpiece (1) for ultrasonic electro-medical apparatuses includes a grip, which carries an operating tip for treatment on a patient and which consists of two portions, having electric and hydraulic connections. The two portions are removably screw-coupled.

11 Claims, 2 Drawing Sheets

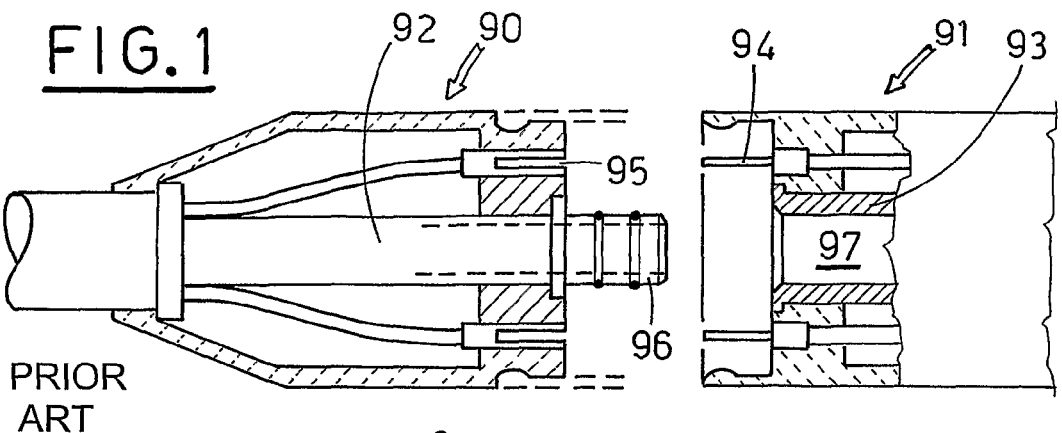
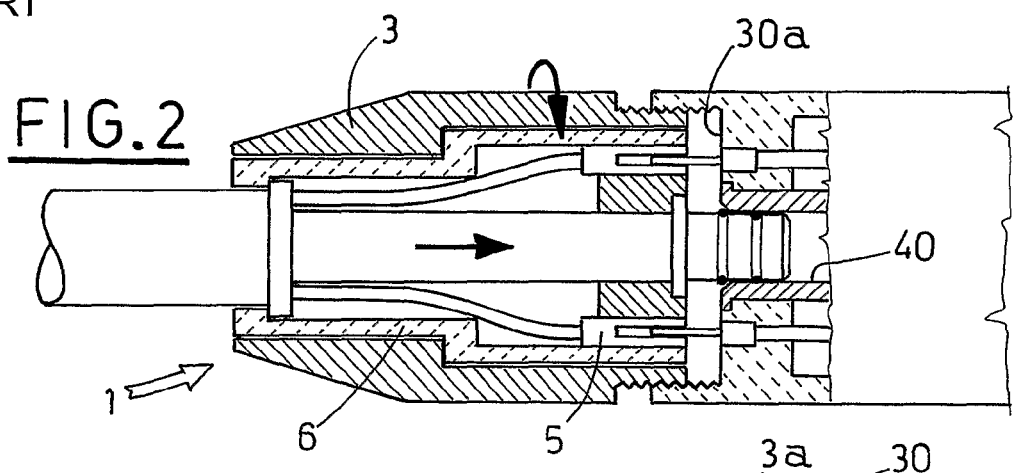
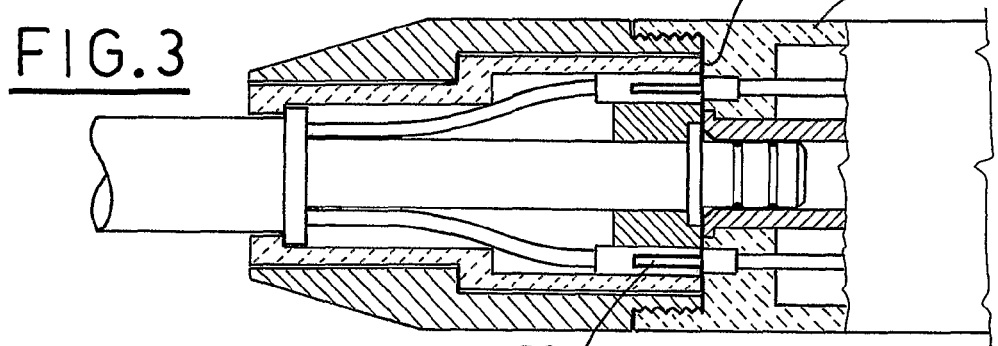
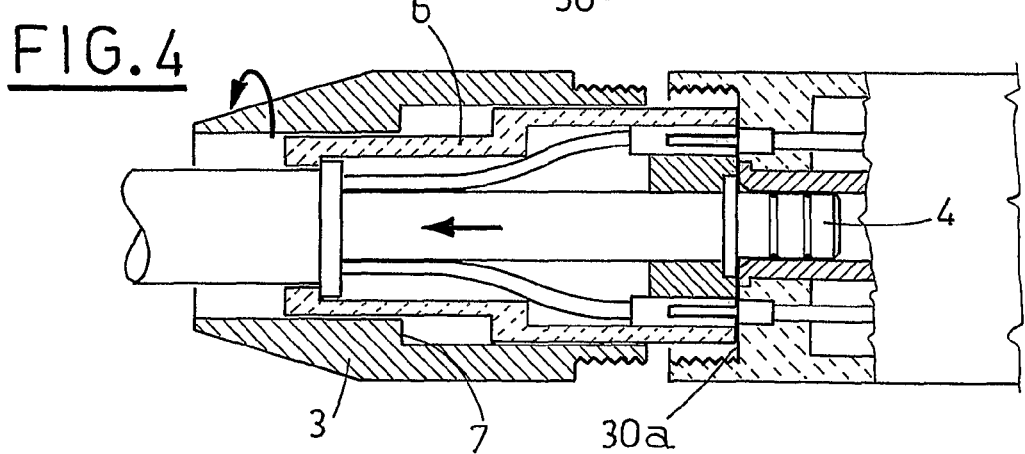

US 8,226,564 B2

HANDPIECE FOR ULTRASONIC ELECTRO-MEDICAL APPARATUSES

FIELD OF THE INVENTION

The present invention relates to ultrasonic electromedical apparatuses, with particular reference to a handpiece for such apparatuses.

BRIEF DESCRIPTION OF PRIOR ART

The field of ultrasonic electro-medical apparatuses, e.g. for maxillo-facial applications and/or for treatment of dermal ulcers use handpieces substantially formed by a grip, designed for taking hold by the operator, which ends with a shaft, having an operating tip connected thereto removably, for treatment on a patient in a prefixed operation area.

The operating tip, operated by an ultrasonic piezoelectric transducer situated inside the grip, identifies substantially two sections, namely a transmission section and an operating section, connected to the grip and to the patient's operation area, respectively, which form therebetween a working angle, usually included between 0° and 90°.

The handpiece is connected to an electronic pulse generator, provided with adjustment means, which generates electric pulses sent to the ultrasonic transducer by a flexible cable, including also at least one flexible hose for adduction of a sterile liquid, to ensure the patient's operation area being wet.

The liquid is fed from a tank, e.g. a disposable bag, downstream of which there is a peristaltic pump.

The sterile liquid passes through one or more ducts made in the grip and other ducts made in the operating tip, so as to be directed, at a prefixed pressure, to the patient's operation area.

Generally, the sterile liquid flowing ducts are situated inside both in the grip and in the operating tip.

However, there are uses, in which the sterile liquid flowing ducts may be situated outside the grip and/or the operating tip.

In most cases, the handpieces used in the ultrasonic electromedical apparatuses have one-piece grips, with the sterile liquid flowing ducts and electric connections for supplying the ultrasonic piezoelectric transducer situated thereinside.

This construction of the handpiece makes its decontamination between two subsequent uses extremely difficult, because the sterilization chamber must house both the handpiece and its flexible cable for connection to the ultrasonic generator, which is particularly bulky.

FIG. 1 shows a known handpiece made in two portions 90, 91, which can be snap-fit coupled (shown schematically with broken line).

Each of the two portions has corresponding liquid flowing ducts 92, 93 and cables for electric supply of the piezoelectric transducer.

At the heads of the portions 90, 91, the electric terminals include a pair of pins 94, which enter the corresponding sockets 95, while the fluid terminals, provided with seals, include a sleeve 96, which enters a relative seat 97.

The above construction of the handpiece allows easy decontamination steps, because it is possible to introduce only the operating tip portion into the sterilization chamber, avoiding the introduction of the flexible cable for connection to the ultrasonic generator, which is particularly bulky.

However, an important drawback of the so obtained handpiece lies in the snap coupling instability, which can lead to unintentional uncoupling of the two portions, especially due to the generated ultrasonic vibrations.

SUMMARY OF THE INVENTION

The object of the present invention is to avoid the above mentioned drawbacks by proposing a handpiece for ultrasonic electro-medical apparatuses, particularly indicated for maxillo-facial applications and/or for treatment of dermal ulcers, which allows high reliability and functionality standards during any working step.

A further object of the present invention is to propose a handpiece, which permits particularly rapid and easy sterilization operations.

Another object of the present invention is to propose an extremely versatile, relatively cheap handpiece, which requires particularly simple and rapid maintenance operations.

The above mentioned objects are obtained, in accordance with the contents of the claims, by the handpiece for ultrasonic electro-medical apparatuses, of the type including

BRIEF DESCRIPTION OF THE FIGURES

The characteristic features of the invention will be pointed out in the following description of some preferred, but not exclusive embodiments, with reference to the enclosed figures, in which:

FIG. 1 is a schematic, axial section view of a handpiece of prior art;

FIGS. 2, 3, 4 are schematic, axial section views of the proposed handpiece, according to a preferred embodiment, in subsequent operation steps;

DESCRIPTION OF THE PREFERRED EMBODIMENTS OF THE INVENTION

Figure 5:
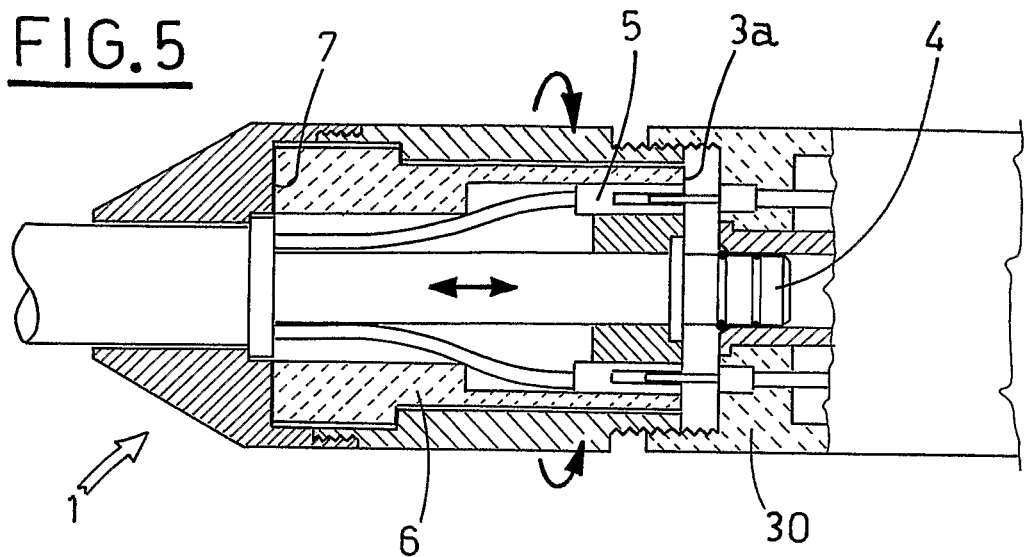
FIGS. 5, 6 are schematic, axial section views of the proposed handpiece, according to another embodiment, in subsequent operation steps.

With reference to the above described Figures, the general reference numeral 1 indicates the proposed handpiece for ultrasonic electromedical apparatuses, particularly indicated for maxillo-facial applications and for treatment of dermal ulcers, which includes a grip, aimed at carrying an operating tip (not shown) for treatment on a patient, and including two portions, first 3 and second 30, aimed at coupling removably.

In known way, each portion 3, 30 of the handpiece 1 grip has electric and fluid connections, respectively for electric supply of an ultrasonic transducer (not shown), cooperating with the operating tip, and for adducing a sterile liquid to be sprayed onto the patient's operation area.

In particular, the heads 3a, 30a of the respective portions 3, 30 have relative terminals, hydraulic 1, 40 and electric 5, 50, which assure the hydraulic and electric continuity, when the portions 3, 30 are coupled.

For example, the fluid terminals include a sleeve 4 and a relative seat 40, receiving the latter, when the portions 3, 30 are coupled, while the electric terminals include a pair of pins 50 and a corresponding pair of sockets 5.

The proposed handpiece 1 includes, in an innovative way a tubular element 6, freely introduced e.g. into the first portion 3, and having a head, to which the fluid terminals 4 and electric terminals 5 of the same first portion 3 are connected, so as to allow the latter to rotate with respect to the tubular element 6, when the portions 3, 30 are coupled.

The tubular element 6, freely introduced into the first portion 3, provides a screw connection of the grip portions 3, 30.

Advantageously, the handpiece 1 includes means for axial abutment of the tubular element 6, e.g. connected to the first portion 3.

The abutment means include, for example, at least one first ring-like shoulder 7, formed by the inner area of the first portion 3, against which the tubular element 6 can go axially in abutment (FIGS. 2, 3, 4).

In particular, the first ring-like shoulder 7 is defined by a variation of the first portion 3 inner diameter, which forms a stepped area therein.

Figure 6:
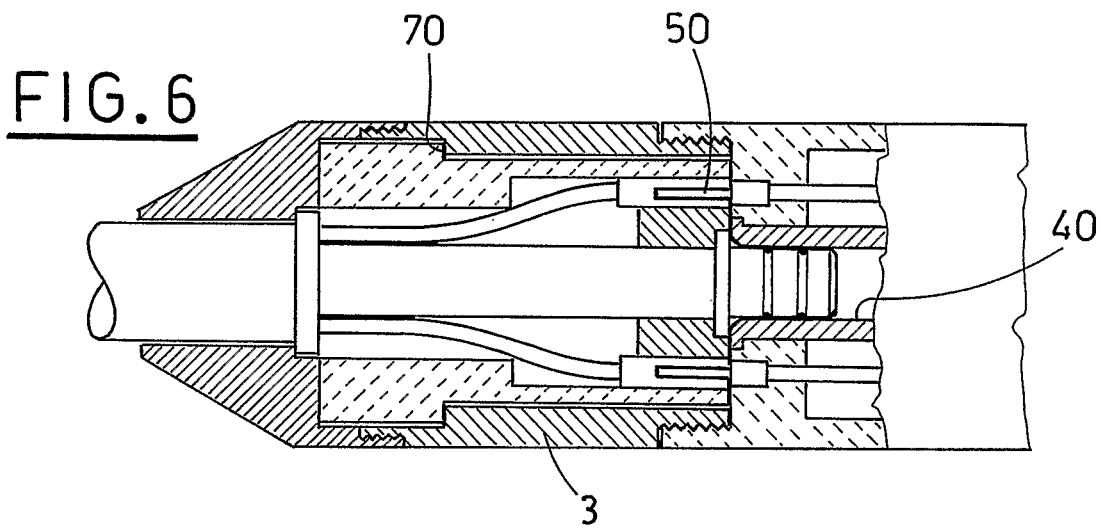
Figure 7:
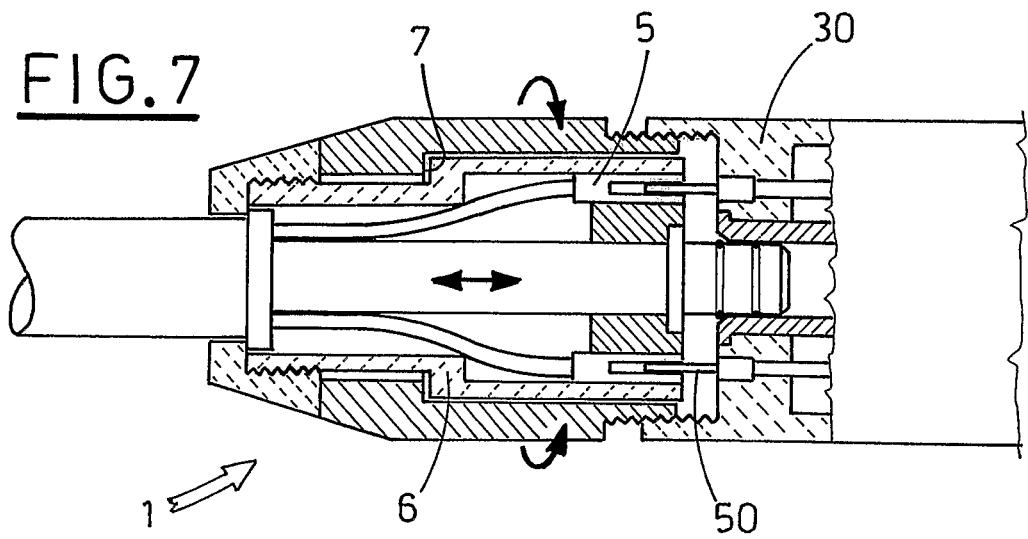
FIG. 7 is a schematic, axial section view of the proposed handpiece, according to a further embodiment, in a particularly significant operation step.

According to another embodiment, the abutment means include a pair of ring-like shoulders, first 7 and second 70, which can prevent the tubular element 6 from axial translation (FIGS. 5, 6, 7).

Specifically, with reference to FIGS. 5 and 6, the pair of ring-like shoulders 7, 70 includes a collar, made in the tubular element 6 and engaging with a corresponding circumferential groove, made in the inner area of the first portion 3, leaving a clearance.

In this case, the first portion 3 of the grip includes two sections, aimed at coupling removably, e.g. by screw connection, in order to allow the introduction or removal of the tubular element 6 into/from the first portion 3, thus engaging and/or releasing the tubular element 6 with/from the pair of ring-like shoulders 7, 70.

Likewise, with reference to FIG. 7, the pair of ring-like shoulders 7, 70 can include a circumferential groove, made in the tubular element 6, which engages, leaving a with clearance, with a corresponding collar made in the inner area of the first portion 3.

In this case, the tubular element 6 includes two sections, aimed at coupling removably, e.g. by threading, in order to allow the tubular element 6 to engage and/or disengage with/from the first corresponding portion 3.

It is clearly understood from the above description how the proposed handpiece for ultrasonic electro-medical apparatuses, particularly indicated for maxillo-facial applications and/or for treatment of dermal ulcers, allows to obtain high reliability and functionality standards in any working step, avoiding any accidental disengaging of the portions of the handpiece grip.

The screw connection between the two portions forming the grip prevents any accidental disengaging, caused especially by ultrasonic vibrations.

In particular, the screw connection is possible due to the free positioning of the tubular element in the first portion, which allows the latter to rotate with respect to the tubular element, thus permitting to obtain easily the electric and fluidic continuity.

The possibility of dividing the grip in two or more portions ensures particularly rapid and easy sterilization steps.

The handpiece grip, including basically two portions and a tubular element freely introduced into one of them, allows the maximum accessibility of the handpiece, thus making the maintenance operations particularly simple and rapid.

The invention claimed is:

1. A handpiece for ultrasonic electro-medical apparatuses comprising:
    a grip, for holding the handpiece, said grip consisting of at least two portions, namely a first portion (3) and a second portion (30) threadably coupled removably to each other with a screw connection;
    an operating tip, for performing a treatment on a patient, said operating tip being connected to said grip;
    first electric terminals and first fluidic terminals provided in said first portion (3) and second electric terminals and second fluidic terminals provided in said second portion (30), respectively for coupling together for supplying power to an ultrasonic transducer cooperating with the operating tip, and for supplying a sterile liquid to be sprayed on a patient's operation area;
    a tubular element (6), freely rotatably mounted within one of said first and second portions (3, 30), said tubular element having a head carrying said fluid terminals (4) and electric terminals (5) of said one of said first and second portions, so that said tubular element containing portion is freely rotatable with respect to the tubular element (6) and said tubular element containing portion can be rotatably disconnected from the non-tubular element containing portion while said fluid terminals and electric terminals contained within said head of said tubular element remain aligned with the fluid terminals and electric terminals provided in the non-tubular element containing portion wherein said tubular element containing portion has axial abutment means for limiting axial movement of said tubular element (6); and,
    wherein said abutment means include at least one ring-like shoulder (7), which is formed by an inner stepped area provided in the tubular element containing portion and against which said tubular element (6) goes in abutment axially.

2. A handpiece, as claimed in claim 1, wherein said at least one ring-like shoulder (7) is defined by a variation of an inner diameter of said tubular element containing portion, forming said stepped area.

3. A handpiece, as claimed in claim 1, wherein said at least one ring-like shoulder (7) of said abutment means faces a second ring-like shoulder (70), with the tubular element having a portion located therebetween which prevents axial translation of the tubular element (6).

4. A handpiece, as claimed in claim 1, wherein said tubular element containing portion includes a first section having the at least one ring-like shoulder therein, and a second section having a second ring-like shoulder facing the at least one ring-like shoulder, the first section and second sections being removably coupled together, so that the coupling of the first section and the second section locates a portion of the tubular element therebetween.

5. A handpiece, as claimed in claim 4, wherein said at least one ring-like shoulder and said second ring-like shoulder form a circumferential groove for receiving the portion of the tubular element in the form of a collar therein.

6. A handpiece, as claimed in claim 1, wherein said tubular element receiving portion is composed of a pair of sections, which couple removably, for permitting assembly with the tubular element.

7. A handpiece, as claimed in claim 1, wherein one of said first fluid terminals or second fluid terminals (4, 40) is a sleeve and the other of the first fluid terminals or second fluid terminals for coupling therewith is a corresponding seat.

8. A handpiece, as claimed in claim 1, wherein one of said first electric terminals or second electric terminals (5, 50) is a pair of pins and the other of the first electric terminals or second electric terminals for coupling therewith is a corresponding pair of sockets for receiving the pins therein.

9. A handpiece for ultrasonic electro-medical apparatuses comprising:
    a grip, for holding the handpiece, said grip consisting of at least two portions, namely a first portion (3) and a second portion (30) threadably coupled removably to each other with a screw connection;
    an operating tip, for performing a treatment on a patient, said operating tip being connected to said grip;
    first electric terminals and first fluidic terminals provided in said first portion (3) and second electric terminals and second fluidic terminals provided in said second portion (30), respectively for coupling together for supplying power to an ultrasonic transducer cooperating with the operating tip, and for supplying a sterile liquid to be sprayed on a patient's operation area;

a tubular element (6), freely rotatably mounted within one of said first and second portions (3, 30), said tubular element having a head carrying said fluid terminals (4) and electric terminals (5) of said one of said first and second portions, said tubular element containing portion being freely rotatable with respect to the tubular element (6) so that said tubular element containing portion can be rotatably disconnected from the non-tubular element containing portion while said fluid terminals and electric terminals contained within said head of said tubular element remain aligned with the fluid terminals and electric terminals provided in the non-tubular element containing portion;

wherein said tubular element has axial abutment means for limiting axial movement of said tubular element containing portion; and, wherein said tubular element consists of a first section which includes a first ring-like shoulder, a second section which includes a second ring-like shoulder that faces the first ring-like shoulder, the first section and second sections being removably coupled together, so that the coupling of the first section and the second section locates a portion of the tubular element containing portion therebetween.

10. A handpiece, as claimed in claim 9, wherein one of said first fluid terminals or second fluid terminals (4, 40) is a sleeve and the other of the first fluid terminals or second fluid terminals for coupling therewith is a corresponding seat.

11. A handpiece, as claimed in claim 9, wherein one of said first electric terminals or second electric terminals (5, 50) is a pair of pins and the other of the first electric terminals or second electric terminals for coupling therewith is a corresponding pair of sockets for receiving the pins therein.

* * * * *